(12) United States Patent
Schick

(10) Patent No.: US 9,211,052 B2
(45) Date of Patent: Dec. 15, 2015

(54) MEASURING ENDOSCOPE

(75) Inventor: Anton Schick, Velden (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 730 days.

(21) Appl. No.: 13/499,500

(22) PCT Filed: Sep. 29, 2010

(86) PCT No.: PCT/EP2010/064457
§ 371 (c)(1),
(2), (4) Date: Mar. 30, 2012

(87) PCT Pub. No.: WO2011/039254
PCT Pub. Date: Apr. 7, 2011

(65) Prior Publication Data
US 2012/0188353 A1     Jul. 26, 2012

(30) Foreign Application Priority Data

Sep. 30, 2009 (DE) .......................... 10 2009 043 538

(51) Int. Cl.
*A61B 1/00* (2006.01)
*A61B 1/06* (2006.01)
*G01B 11/12* (2006.01)
(Continued)

(52) U.S. Cl.
CPC ........... *A61B 1/00096* (2013.01); *A61B 1/0607* (2013.01); *A61B 1/0623* (2013.01); *G01B 11/12* (2013.01); *G01B 11/25* (2013.01); *G02B 23/2423* (2013.01); *G02B 23/2461* (2013.01)

(58) Field of Classification Search
CPC ............ A61B 1/00096; A61B 1/0607; A61B 1/0623; G01B 11/12; G01B 11/25; G01B 23/2423; G01B 23/2461
USPC ............................................... 348/74, E7.085
See application file for complete search history.

(56) References Cited

U.S. PATENT DOCUMENTS 5,050,974 A * 9/1991 Takasugi et al. .............. 359/728
5,278,642 A * 1/1994 Danna et al. .................... 348/70
5,372,502 A 12/1994 Massen et al.
(Continued)

FOREIGN PATENT DOCUMENTS

DE      38 29 925 A1    3/1990
DE     295 06 021 U1    5/1995
(Continued)

OTHER PUBLICATIONS

International Search Report of PCT/EP2010/064457, Dated Dec. 30, 2010.
(Continued)

*Primary Examiner* — Sath V Perungavoor
*Assistant Examiner* — Peter D Le
(74) *Attorney, Agent, or Firm* — Laurence Greenberg; Werner Stemer; Ralph Locher

(57) ABSTRACT

An endoscope measures the topography of a surface. The endoscope contains a projection unit and an imaging unit. The endoscope is characterized in that an objective unit is provided as a component both of the projection unit and the imaging unit. By the integration of the projection unit and the imaging unit, which both use a common objective unit, the structural volume required by both units is reduced resulting in a smaller endoscope.

7 Claims, 2 Drawing Sheets

(51) Int. Cl.
*G01B 11/25* (2006.01)
*G02B 23/24* (2006.01)

(56) References Cited

U.S. PATENT DOCUMENTS

| | | | |
|---|---|---|---|
| 6,332,092 B1 | 12/2001 | Deckert et al. | |
| 6,887,196 B2 | 5/2005 | Arai et al. | |
| 8,040,527 B2 | 10/2011 | Kunz et al. | |
| 2002/0007111 A1 | 1/2002 | Deckert et al. | |
| 2003/0164952 A1 | 9/2003 | Deichmann et al. | |
| 2003/0191369 A1 | 10/2003 | Arai et al. | |
| 2006/0069314 A1* | 3/2006 | Farr | 600/179 |
| 2008/0269563 A1* | 10/2008 | Takahashi | 600/178 |
| 2009/0292168 A1* | 11/2009 | Farr | 600/109 |
| 2010/0020333 A1 | 1/2010 | Kunz et al. | |
| 2010/0060718 A1 | 3/2010 | Forster et al. | |
| 2010/0195007 A1* | 8/2010 | Takahashi | 349/16 |
| 2011/0285995 A1* | 11/2011 | Tkaczyk et al. | 356/326 |
| 2012/0190923 A1 | 7/2012 | Kunz et al. | |

FOREIGN PATENT DOCUMENTS

| | | |
|---|---|---|
| DE | 198 03 679 A1 | 8/1999 |
| DE | 200 05 842 U1 | 9/2000 |
| DE | 101 04 483 A1 | 10/2002 |
| DE | 603 06 235 T2 | 5/2007 |
| DE | 10 2006 054 310 A1 | 5/2008 |
| DE | 10 2007 005 388 A1 | 8/2008 |
| JP | 2001064625 A | 3/2001 |
| JP | 2002520647 A | 7/2002 |
| JP | 2008514304 A | 5/2008 |
| JP | 2008289863 A | 12/2008 |
| JP | 2013506861 A | 2/2013 |

OTHER PUBLICATIONS

German Patent and Trademark Office, Office Action Dated Aug. 2, 2010.

* cited by examiner

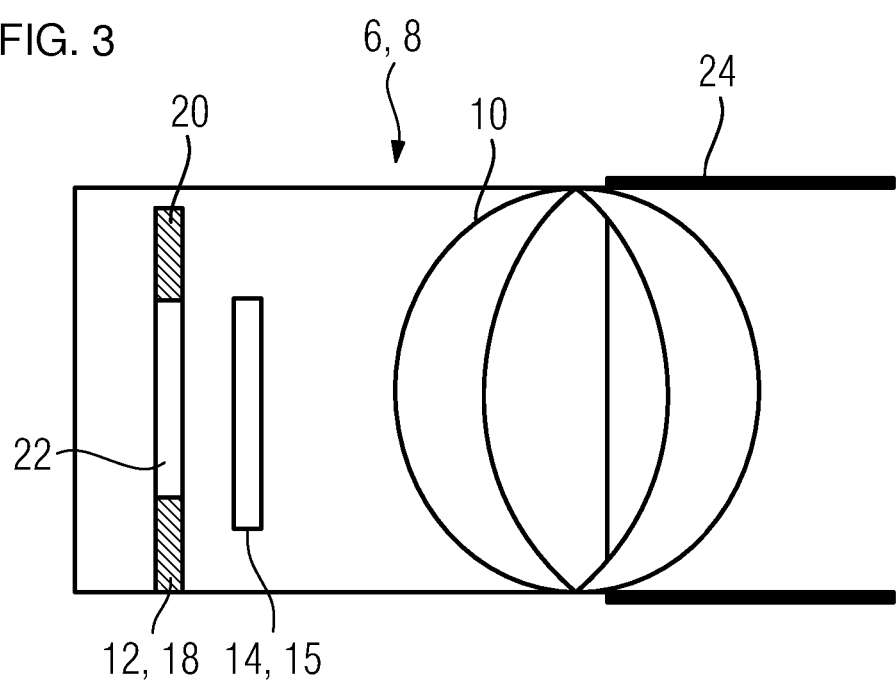

MEASURING ENDOSCOPE

BACKGROUND OF THE INVENTION

Field of the Invention

The invention relates to an endoscope for measuring the topography of a surface, and a method for measuring the topography of a surface.

Conventional and well-researched techniques for measuring three-dimensional geometries are often based on active triangulation. However, in confined environments, such as human auditory canals or in bore holes, it becomes ever more difficult to implement triangulation as such. Particularly in the field of measuring endoscopy, it is not easy to achieve the spatial arrangement of transmitting and receiving units or to position projection and imaging units at the appropriate angles. It is also not usually possible to record relatively longer or larger hollow chambers in one image. This means that it is necessary to measure spatially overlapping regions three-dimensionally chronologically one after another in order subsequently to combine said images into a 3D representation using data processing (3D data sticking). The larger the overlapping regions are, the more precisely the linking of individual recordings in 3D space can be achieved. This presupposes that the individual recordings themselves have as many measuring points as possible in fixed relationship to one another.

BRIEF SUMMARY OF THE INVENTION

It is an object of the invention to provide an endoscope for measuring surface topographies, which occupies less space in relation to the prior art and is able, for example when using active triangulation, to record relatively large measurement regions.

The endoscope according to the invention for measuring the topography of a surface has a projection unit and an imaging unit. The endoscope is characterized in that an objective unit is provided which is both a component of the projection unit and also of the imaging unit.

By means of an integrated configuration of the projection unit and the imaging unit, which both use a common objective unit, the structural volume required by both units, the imaging units and the imaging units with the projection unit can be significantly reduced, leading thereto that the endoscope can also be designed smaller. Furthermore, given a similar structural size for measuring the topography of the surface, larger measurement regions can be recorded.

In a further embodiment of the invention, the projection unit comprises a projection structure and the imaging unit comprises an imaging medium. The imaging medium and the projection structure are preferably disposed centrally to an optical axis. This measure also contributes to saving structural volume.

In a preferred embodiment of the invention, the projection structure is configured in the form of a transparency. The projection structure, or in the special form, the transparency, has, in an external region thereof, concentric colored rings. The concentric colored rings serve for color coding and result in different colored projection rays, the reflection pattern of which allows conclusions be drawn regarding the topography and character of the surface.

In a further embodiment of the invention, the projection structure has a central region which is covered relative to the optical axis by the imaging medium. Usually, in this central region of the projection structure, in particular of the transparency, no concentric colored rings are provided. This zone of the projection structure which is free from colored rings can be used to accommodate the imaging medium on the same optical axis in a space-saving manner. The imaging medium and the projection structure can essentially lie in one plane, but can also be displaced parallel to one another relative to the optical axis.

Furthermore, in another embodiment of the invention, the projection unit has, adjacent to the objective unit, an annular mirror lens which is rotationally symmetrical relative to the optical axis. Said annular mirror lens enables projection rays to be deflected differently than the imaging rays arriving through the objective unit. It is expedient in this case for projection rays to pass through the objective unit and be deflected by the annular mirror lens. By contrast, imaging rays reflected from the surface—i.e. reflected projection rays—and impinging upon the objective unit are not deflected by the annular mirror lens. The annular mirror lens therefore allows projection rays and imaging rays to be deflected into a different ray path.

Further advantageous embodiments of the invention are described below based on the following figures, in which:

BRIEF DESCRIPTION OF THE SEVERAL VIEWS OF THE DRAWING

FIG. 3 shows an arrangement of lenses, imaging medium and projection structure in the combined imaging unit-projection unit.

DESCRIPTION OF THE INVENTION

Figure 1:
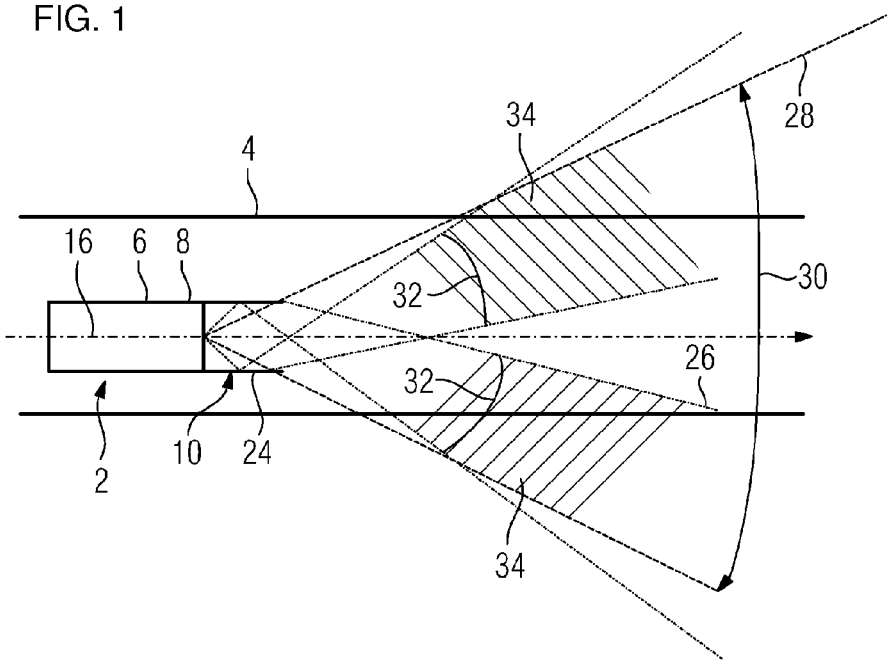
FIG. 1 shows a schematic representation of a projection unit and an imaging unit of an endoscope with a suitable ray path.

FIG. 1 shows a schematic representation of an endoscope 2 (shown here without an endoscope external wall) having a projection unit 6 and an imaging unit 8. Schematic ray paths of projection rays 26 and imaging rays 28 are also shown. The projection unit 6 and the imaging unit 8 are integrated in such a manner that both the projection unit and the imaging unit comprise an overall objective unit 10 (see FIG. 2). Furthermore, the projection unit 6 has an annular mirror lens 24 which serves to deflect projection rays 26.

In FIG. 1, projection rays 26 are shown with a dotted and dashed line, whilst imaging rays 28 are shown with a dashed line. The dashed lines 28 and the dotted and dashed lines 26 each show the outer limit of a projection region 32 or a field of view 30.

In the representation in FIG. 1, the optical system used results in two projection regions 32 and a field of view 30. In order to measure the topography of the surface 4, which is also shown schematically here as a cylindrical channel, the triangulation method is used. For this purpose, the projection rays 26, which possibly comprise different color spectra (see below), are emitted by the projection unit 6. Said projection rays 26 impinge upon the surface 4 and are reflected therefrom. The reflected projection rays are designated imaging rays 28. The imaging unit accepts and guides the imaging rays to an imaging medium which also serves for evaluating the imaging rays.

The region which is enclosed by both the projection rays 26 or the projection region 32 and by the field of view 30 is designated the measurement region 34. The measurement region 34 is therefore the region in which the projection region 30 and the field of view 32 intersect. Measurement by the triangulation method can only be carried out in the region in which projection rays 26 and the field of view 30 intersect. The larger the measurement region 34 is configured, the larger is the region in which a measurement can be carried out. Particularly in confined hollow spaces, it is often difficult, using known methods, to configure the field of projected rays 26 (projection region 32) and the field of view 30 such that an adequately large measurement region 34 is formed.

Figure 2:
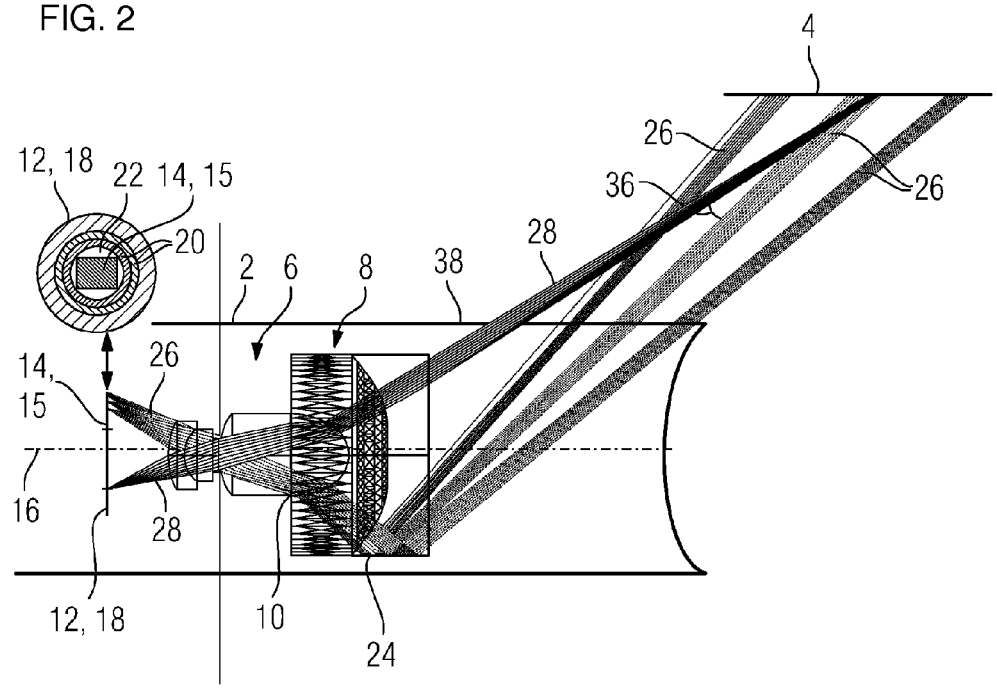
FIG. 2 shows a more detailed representation of the combined projection unit and imaging unit.

FIG. 2 shows a detailed representation of the projection unit 6 and the imaging unit 8 with the common objective unit 10 thereof. The endoscope 2 has an optical axis 16 which extends through the center point of the endoscope 2. In relation to FIG. 2, a viewing direction of the endoscope extends from left to right. A light source (not shown), which is preferably configured in the form of a light waveguide with a collimator optical system or a fiber optic bundle or a light source, for example an LED, emits light rays through a projection structure 12 which, in this case, is configured in the form of a transparency 18. The transparency 18 is configured annular and has concentric color rings 20 in an external region. The transparency 18, which in FIG. 2 is shown as a line in relation to the ray path, is shown again for the sake of clarity, next to FIG. 2 in a plan view.

The light rays which extend through the outer region of the transparency 18 and thus pass through the colored concentric rings are designated projection rays. The projection rays extend through the common objective unit 10, are deflected therein and strike an annular mirror lens 24 arranged upstream of the objective unit 10 or the projection lens system 6. The mirror lens 24 deflects the projection rays 26 laterally with rotation symmetry from one wall 38 of the endoscope 2, after which said rays strike the surface 4 to be investigated. The projection rays 26 are reflected from the surface 4 and, from then on, are designated imaging rays 28. The angle that the projection rays 26 and the imaging rays 28 enclose is designated the triangulation angle 36.

The imaging rays 28 are reflected back and pass, shaded by the mirror lens 24 through the objective unit 10, the objective unit 10 being configured such that non-deflected rays impinge close to the center in relation to the optical axis 16 upon an imaging medium 14 which here takes the form of a sensor chip 15 as used in digital cameras. According to the representation in FIG. 2, the sensor chip 15 and the transparency 18 lie on an optical axis and in one plane. This is a special case, as illustrated in FIG. 3, where the camera chip is arranged at a small distance in front of the transparency. The camera chip 15 is smaller than the transparency 18 and is positioned in a central region of the transparency 18 in relation to the optical axis 16. The central region of the transparency 18 is not filled with colored rings 20 and does not need to be penetrated by the light rays. The arrangement of the sensor chip 15 therefore does not hinder the ray path of the projection rays 28.

The method of triangulation using color coding will now be briefly described. The color structure projected onto an irregular topography of the surface 4 (not shown here) appears, at an observation angle (the triangulation angle) different from the projection angle, to be distorted. The distorted pattern detected by the imaging lens system (the objective unit 10) is imaged on the imaging medium 12. What is produced here is therefore a planar image of the three-dimensional surface.

By means of a suitable evaluation method, the topography of the surface 4 can be calculated by a computer by evaluating the color transitions and the distortion of the color lines. The configuration of the transparency with colored concentric circles is merely one of the advantageous embodiments. This embodiment suggests itself particularly in the case of a light waveguide having a circular cross-section. Other encoding patterns, such as linear patterns, can essentially also be used.

FIG. 3 again shows a somewhat enlarged schematic representation which illustrates the combined projection unit 6 and imaging unit 8. From left to right, firstly the transparency 18 is to be seen, which has, in an outer region, concentric colored rings 20; also shown is the central region 22 which is not provided with colored rings. Arranged in front of the transparency 18 is the sensor chip 15. Arranged in front of the sensor chip is the objective unit 10, in front of which is arranged the annular mirror lens 24. The endoscope per se preferably consists of a transparent glass which is suitable for allowing the projection rays 26 to emerge at the endoscope wall 38. A transparent plastics material can also serve as a suitable endoscope material. The endoscope usually has a diameter in the range of 3 mm to 5 mm. The combined imaging and projection unit 6, 8 usually has a length in the range of 8 mm to 12 mm.

Usually, the sensor chip is illuminated at a frequency of 10 Hz to detect the imaging rays 28. The shutter opening time is approximately 10 ms. (The shutter opening time is the time during which imaging rays 28 impinging upon the sensor chip are measured.) This means that at an illumination frequency of 10 Hz, there is a pause of 90 ms between the shutter opening times and that, during this time, the sensor chip recordings are evaluated by calculation software.

The above described arrangement of the measuring endoscope 2 can be applied essentially for all measurements in confined hollow spaces. A particularly advantageous application of the endoscope 2 is in the form of an otoscope, which is introduced into an ear and is used to measure the auditory canal or the ear lobe. The above described "color-coded triangulation" has the advantage, in this regard, that the projection of an encoded color pattern, together with just one image recording of the receiving unit (imaging unit 8) is sufficient to calculate the 3D form of an object. This means that simple projection can be used similarly to transparency projection and that sequential projection of different projection structures is not necessary. This also has the advantage that almost wobble-free freehand scanning by a physician is possible.

Other applications of the endoscope 2 may be found in technical fields. If, for example, for quality-control purposes, bores or other hollow spaces need to be precisely measured, the use of a space-saving endoscope 2 of this type is suitable. For example, in the case of rivet bores which serve for riveting aircraft components, very high demands are placed on the topography of said bores. With an endoscope according to the invention, highly accurate topographical measurements can be made in very confined bores.

The invention claimed is:

1. An endoscope for measuring a topography of a surface, the endoscope comprising:
    a projection unit outputting projection rays;
    an imaging unit receiving imaging rays;
    an objective unit being both a component of said projection unit and also of said imaging unit, said objective unit receiving and conditioning both the projection rays and the imaging rays; and
    said projection unit having an annular mirror lens being rotationally symmetrical relative to an optical axis, said annular mirror lens disposed adjacent to and upstream from said objective unit.

2. The endoscope according to claim 1, wherein:
    said projection unit has a projection structure; and
    said imaging unit has an imaging medium, said projection structure and said imaging medium lie on an optical axis.

3. The endoscope according to claim 2, wherein said projection structure is configured in a form of a transparency.

4. The endoscope according to claim 2, wherein said projection structure has, in an external region thereof, concentric colored rings.

5. The endoscope according to claim 2, wherein said projection structure has a central region covered relative to the optical axis by said imaging medium.

6. The endoscope according to claim 1, wherein the projection rays pass through said objective unit and said annular mirror lens deflects the projection rays.

7. The endoscope according to claim 1, wherein the imaging rays in a form of the projection rays reflected by the surface pass, without deflection at said annular mirror lens, through said objective unit and strike said imaging medium.

* * * * *